United States Patent [19]

Tarr et al.

[11] Patent Number: 5,330,421

[45] Date of Patent: Jul. 19, 1994

[54] TAMPON APPLICATOR

[75] Inventors: Warren Tarr, Turners Falls; William M. Child, Wales; Quiteria M. Mendes, Ludlow, all of Mass.

[73] Assignee: Tambrands Inc., White Plains, N.Y.

[21] Appl. No.: 985,324

[22] Filed: Dec. 4, 1992

[51] Int. Cl.$^5$ .............................................. A61F 13/20
[52] U.S. Cl. ........................................ 604/18; 604/16
[58] Field of Search ................ 604/15, 11, 16, 18, 604/13, 14, 12

[56] References Cited

U.S. PATENT DOCUMENTS

| | | | |
|---|---|---|---|
| 2,355,917 | 8/1944 | Knight | 604/11 |
| 2,829,646 | 4/1958 | Kurkjian | 604/16 |
| 3,101,713 | 8/1963 | Sargent . | |
| 3,124,134 | 3/1964 | Gardner | 604/15 |
| 3,347,234 | 10/1967 | Voss | 604/18 |
| 3,390,671 | 7/1968 | Hildebrand . | |
| 3,534,737 | 10/1970 | Jones, Sr. | 604/18 |
| 3,696,812 | 10/1972 | Jaycox | 604/18 |
| 4,273,125 | 6/1981 | Sakurai . | |
| 4,276,881 | 7/1981 | Lilaonitkul . | |
| 4,286,595 | 9/1981 | Ring . | |
| 4,291,696 | 9/1981 | Ring . | |
| 4,411,647 | 10/1983 | Sakurai et al. | 604/18 |
| 4,413,986 | 11/1983 | Jacobs . | |
| 4,479,791 | 10/1984 | Sprague . | |
| 4,508,531 | 4/1985 | Whitehead | 604/74 |
| 4,543,086 | 9/1985 | Johnson . | |
| 4,573,963 | 3/1986 | Sheldon | 604/15 |
| 4,573,964 | 3/1986 | Huffman | 604/15 |
| 4,610,659 | 9/1986 | Friese | 604/15 |
| 4,676,773 | 6/1987 | Sheldon | 604/14 |
| 4,699,610 | 10/1987 | Hanano et al. . | |
| 4,726,805 | 2/1988 | Sanders | 604/15 |
| 4,891,042 | 1/1990 | Melvin et al. . | |
| 4,911,687 | 3/1990 | Stewart | 604/15 |
| 4,921,474 | 5/1990 | Suzuki et al. | 604/18 |
| 4,960,417 | 10/1990 | Tarr, Jr. et al. | 604/15 |

FOREIGN PATENT DOCUMENTS

| | | |
|---|---|---|
| 0223072 | 5/1987 | European Pat. Off. . |
| 557211 | 5/1958 | Italy ........................... 604/15 |
| 1045962 | 10/1966 | United Kingdom . |
| 2033754B | 5/1980 | United Kingdom . |
| 2060396 | 5/1981 | United Kingdom . |
| 2081586A | 2/1982 | United Kingdom . |
| 2204491A | 11/1988 | United Kingdom . |

Primary Examiner—Paul J. Hirsch
Attorney, Agent, or Firm—Fish & Richardson

[57] ABSTRACT

An insertion device is provided for inserting material into a body cavity is, the material having an enlarged head portion, including an elongate, tubular holder, shaped for insertion into the body cavity and having an expulsion end which is dimensioned to fit over the head portion of the material and adapted to open to allow the material to be expelled therethrough; an elongate, tubular plunger, adapted to hold telescopically at least a portion of the material to be inserted, dimensioned to fit telescopically and slidably within the holder and to be movable from a telescoped position within the holder to an extended position in which one distal end of the plunger is withdrawn from the distal holder, and adapted, in the extended position, to expel the material from the device when pushed manually into the holder; and a retaining structure, interposed between the plunger and the holder and disposed at the expulsion end to engage the head portion of the material and prevent it from moving with the plunger when the plunger is moved from the telescoped to the extended position.

35 Claims, 6 Drawing Sheets

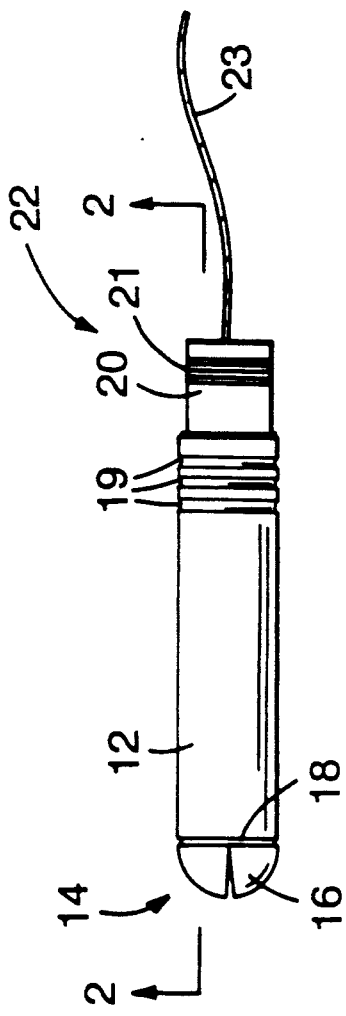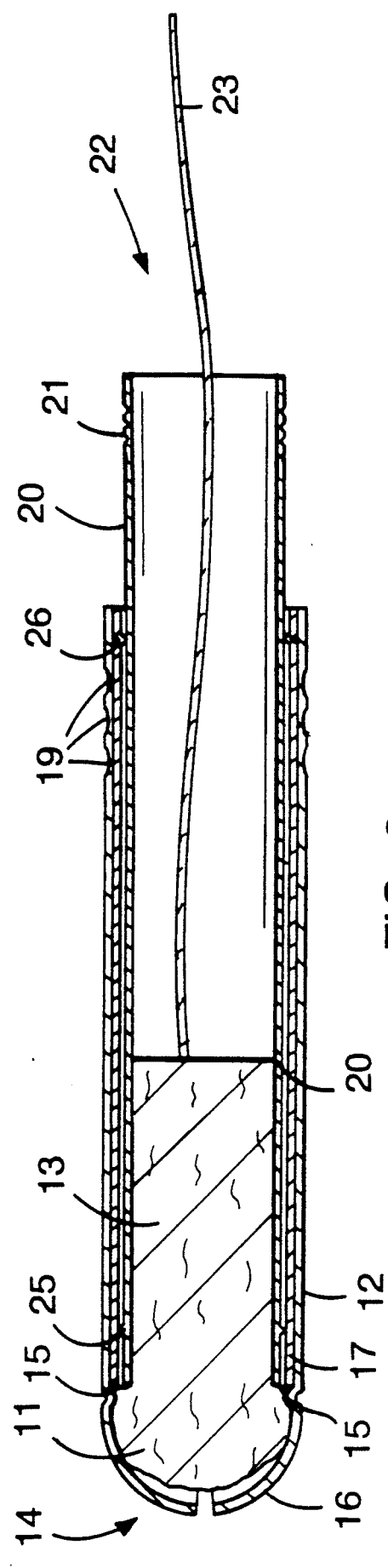

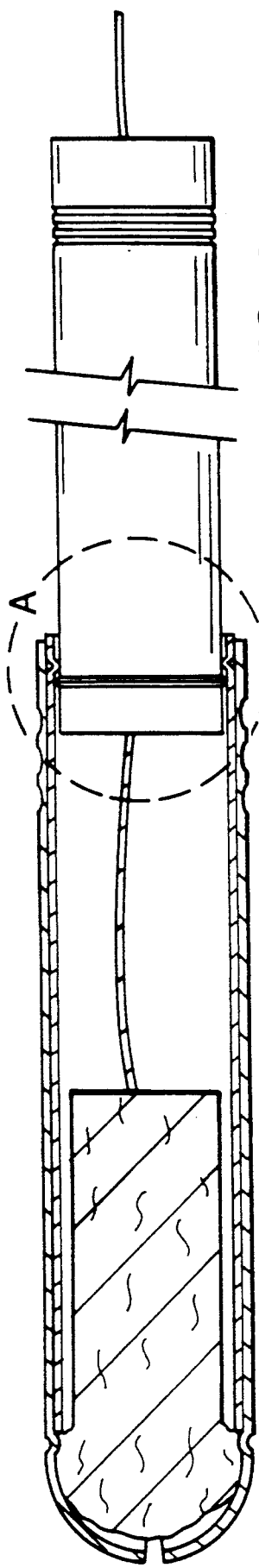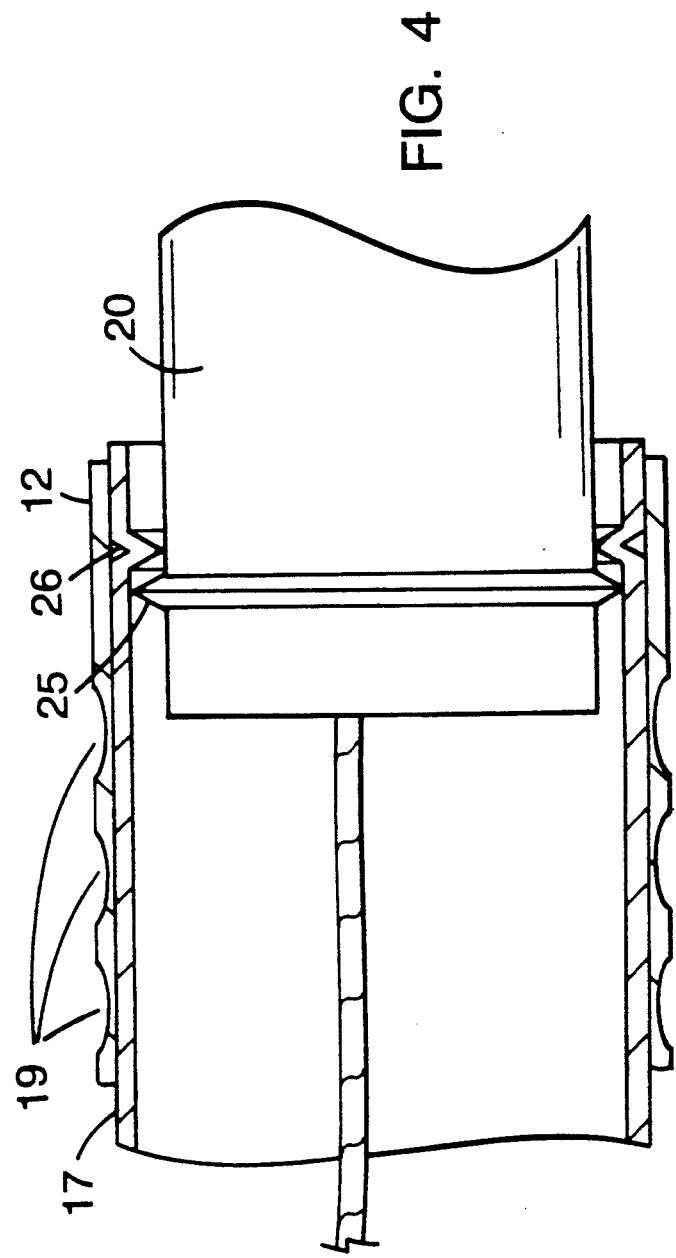

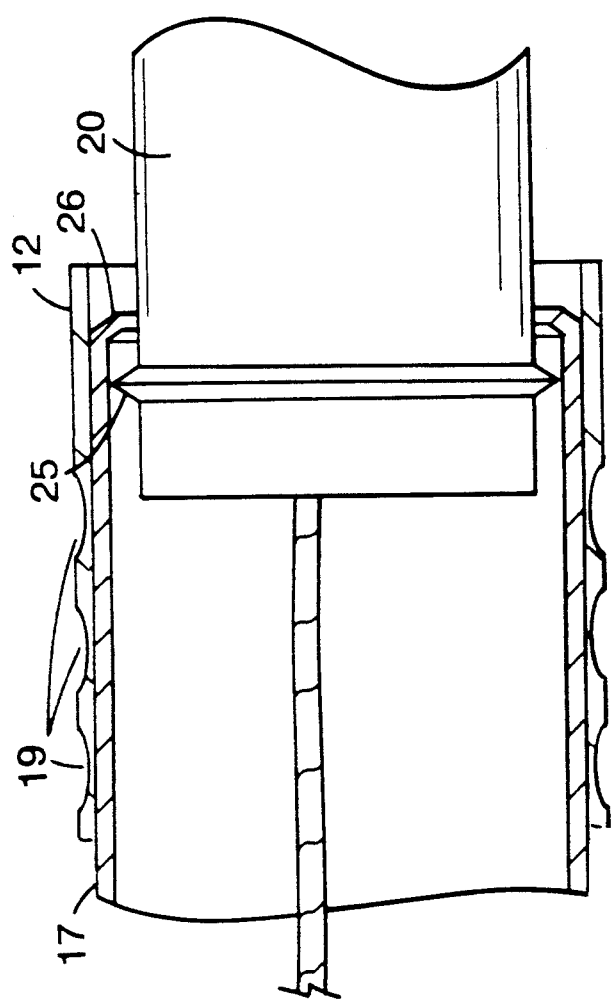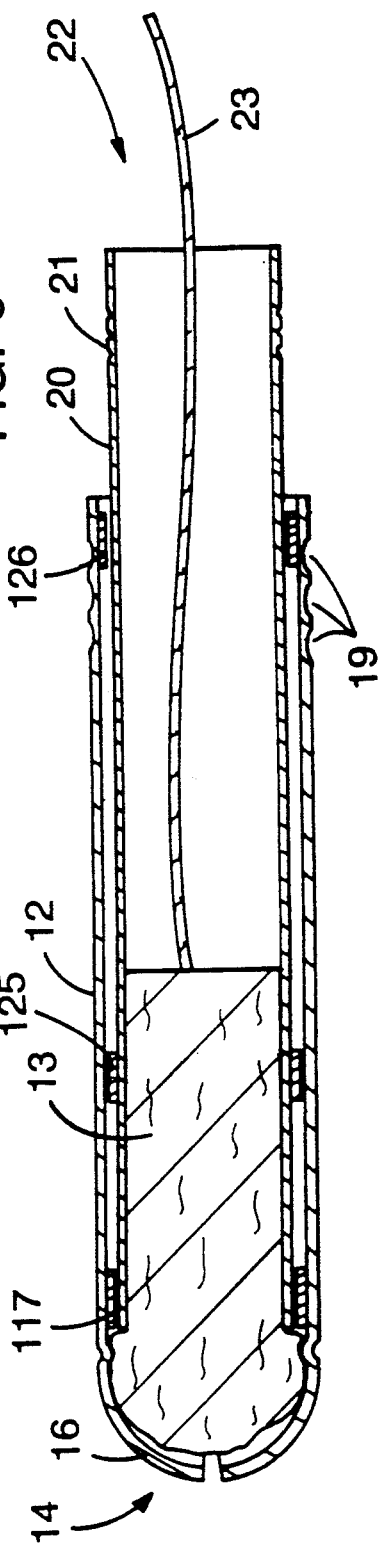

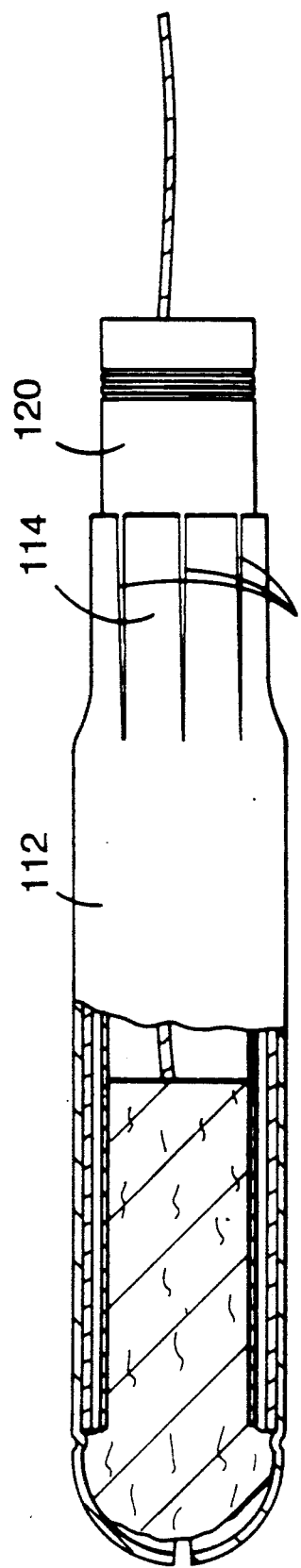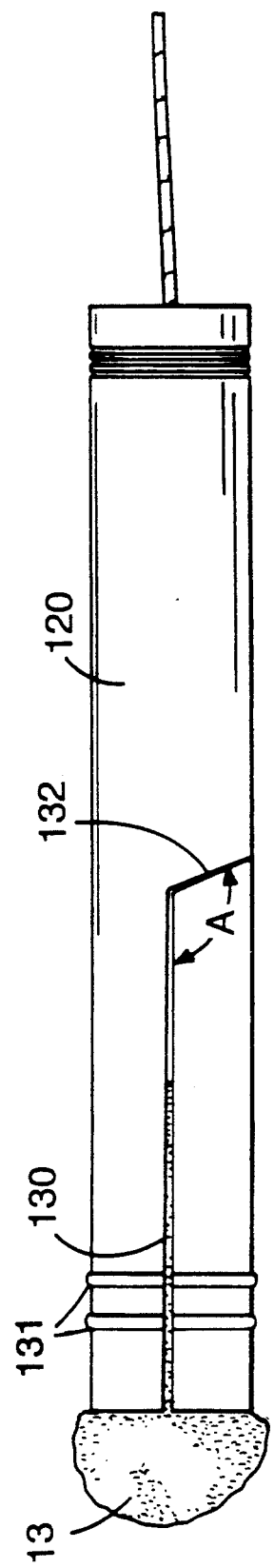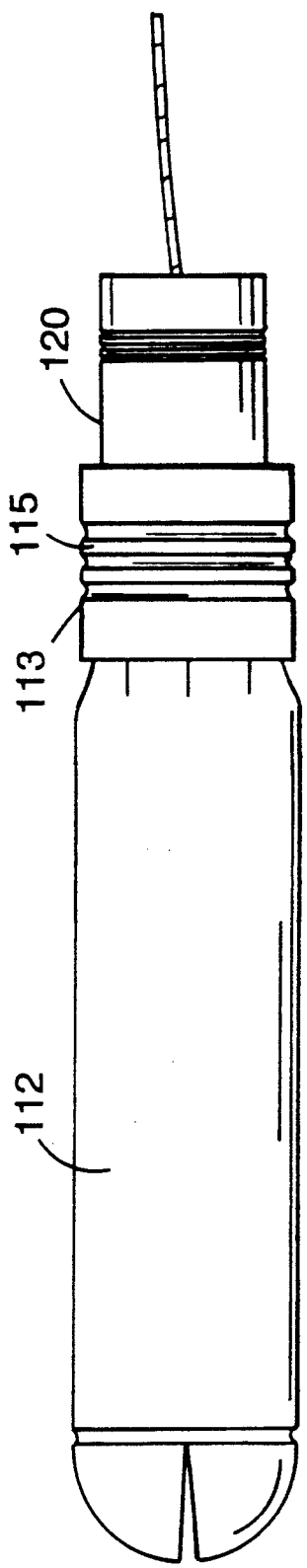

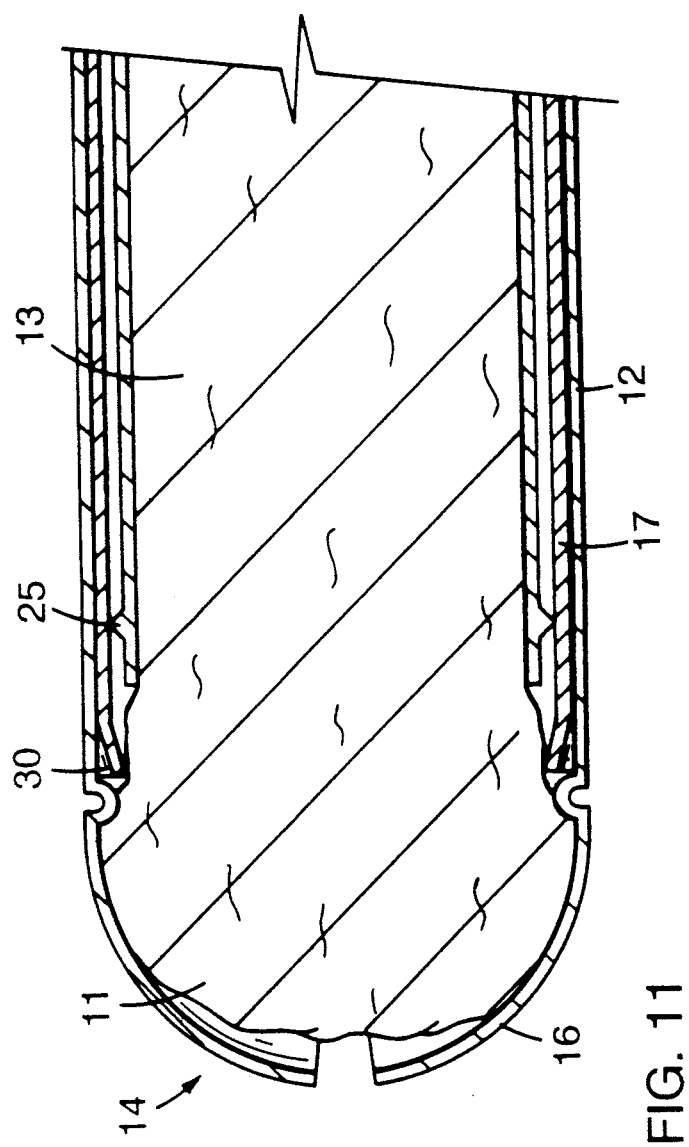
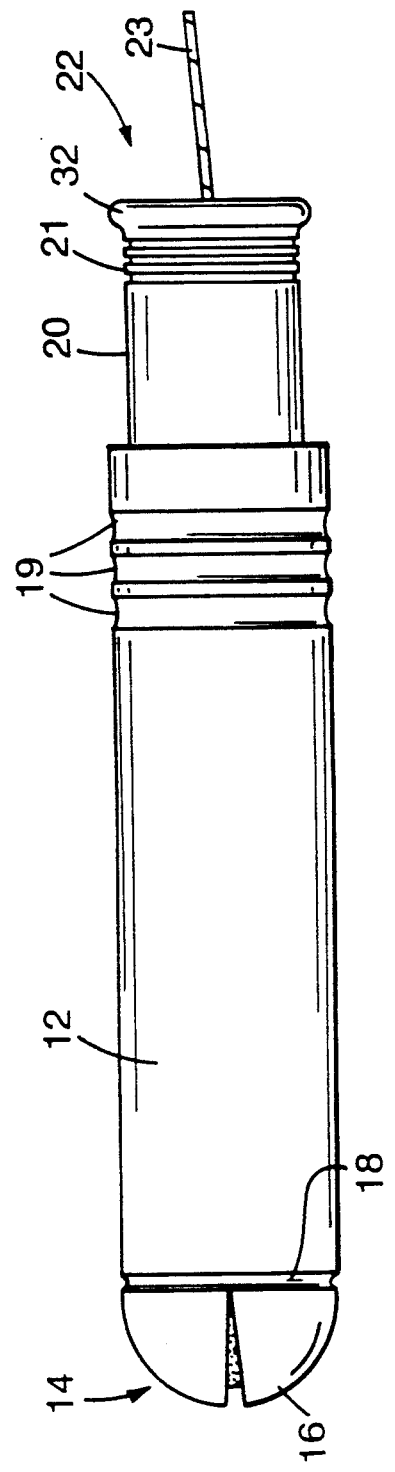
FIG. 11
FIG. 12

TAMPON APPLICATOR

BACKGROUND OF THE INVENTION

This invention relates to a compact insertion device, e.g., a tampon applicator, formed from a paper laminate.

Tampon applicators comprising a pair of telescopically arranged tubes are long known in the art. Some applicators have the tampon exposed at the end intended for vaginal insertion (the expulsion end), while others provide a rounded expulsion end, with the tampon covered by a plurality of "petals" which open during tampon expulsion.

Typically, these applicators comprise a tampon holder tube and a plunger tube, telescopically disposed so that a small portion of the plunger tube is within the holder tube. Such an applicator is thus relatively long, typically about twice the length of the tampon holder tube.

Efforts have been undertaken in the industry to produce a shorter applicator, which would be, e.g., easier to store and transport. Shorter applicators, known in the field as "compact" applicators, are generally formed by disposing most of the length of the plunger tube between the tampon holder tube and the tampon. The plunger tube is withdrawn from the holder tube by the user, prior to insertion. It is thus necessary that the tampon be retained in the holder tube and not withdrawn with the plunger tube. Typically, in closed end applicators this is achieved by a plurality of slots and/or tabs extending from the inner surface of the tampon holder tube to engage the periphery of the "head" of the tampon, thus retaining it in the holder tube. In open end applicators, the head of the tampon itself engages the holder tube and retains the tampon. The provision of slots or tabs for retaining the tampon is disadvantageous, as these structures are difficult to form in paper laminates, which are preferred materials for tampon applicators due to their flushability and biodegradability. Further, in order to form tabs in a paper applicator, it is typically necessary to leave holes, which weaken the applicator and give it an unappealing, flimsy appearance.

SUMMARY OF THE INVENTION

The inventors have found that a compact type laminated paper insertion device, comprising a tubular material holder, and a tubular plunger telescopically disposed in the holder and containing the material to be inserted, can be greatly improved in a variety of respects by providing a retaining structure interposed between the inner wall of the tampon holder tube and the outer wall of the plunger.

In a preferred embodiment, the retaining structure is a tube which extends for approximately the length of the holder, i.e., from the base of the head of the material to be inserted to the distal end of the holder, and is adhered to the inner surface of the holder.

Prior to use, the plunger is retained within the holder, with only a small portion of its distal end extending outside of the holder tube. The material to be inserted, (e.g., a tampon) is retained within the plunger, and has a swelled head portion which extends over, and engages, the retaining structure. When the applicator is to be used, the user pulls the plunger back to an extended position, in which it is positioned to expel the tampon when reinserted into the applicator. By engaging the head of the tampon, the retaining structure thus retains the tampon securely in place while the plunger is being pulled to the extended position.

In a preferred embodiment, either the holder or the retaining tube has a stop, or locking ring, on its inner surface, disposed at the distal end of the holder tube, and the plunger has a corresponding raised area, e.g. ring or c-shaped segment, at its expulsion end, such that the stop and raised area interlock to retain the plunger tube within the holder tube when it is withdrawn prior to use.

In other preferred embodiments, the retaining structure is a ring or C-shaped member adhered to the inner surface of the tampon holder tube, disposed adjacent the head of the tampon to retain the tampon when the plunger tube is withdrawn. In this embodiment, the stop which retains the plunger may be a second ring adhered to the inner surface of the tampon holder tube at its distal end. A third ring is preferably adhered to the plunger, disposed distally of its expulsion end, forming the locking ring which interlocks with the stop. The third ring is located such that the plunger can be withdrawn far enough to completely clear the tampon and pushed forward enough to ensure complete expulsion of the tampon.

In other preferred embodiments, the plunger has an outer diameter smaller than the outer diameter of the tampon, and is slitted to allow the tampon to be retained therein; and the retaining tube has an inwardly folded tab at its distal end which causes the plunger and/or tampon, preferably the plunger, to move off center during expulsion, preventing repositioning of the plunger around the tampon.

In a second aspect, the invention features an insertion device for inserting material into a body cavity, comprising an elongate, tubular holder, shaped for insertion into the body cavity and having an expulsion end of a first diameter, which is dimensioned to fit over the head portion of the material and adapted to open to allow the material to be expelled therethrough, and a distal end having a plurality of lengthwise slots defining a plurality of strips which, when urged together, form a portion having a second diameter, smaller than the first diameter; a closing ring (e.g., formed of paper or tape), surrounding the portion and retaining the strips together; and an elongate, tubular plunger, adapted to hold telescopically at least a portion of the material to be inserted, dimensioned to fit telescopically and slidably within the holder and to be movable from a telescoped position within the holder to an extended position in which one distal end of the plunger is withdrawn from the distal holder, and adapted, in the extended position, to expel the material from the device when pushed manually into the holder. The closing ring provides a secure and effective means of joining the strips together and preventing their becoming separated during use. Additionally, the closing ring provides a finger grip area.

In preferred embodiments, the material is a tampon and the holder is shaped for vaginal insertion; the device further includes a retaining structure, interposed between the plunger and the holder and disposed at the expulsion end to engage the head portion of the material and prevent it from moving with the plunger when the plunger is moved from the telescoped to the extended position; the plunger has an outer diameter smaller than the outer diameter of the tampon, and is slitted to allow the tampon to be retained therein; the slit extends longitudinally from the expulsion end of the plunger toward the distal end of the plunger, defining a longitudinal region; an angled region of the slit extends from the distal end of the longitudinal region circumferentially around the plunger; and the angle formed between the longitudinal region and the angled region of the slit is at least 90 degrees.

In another aspect, the invention features an insertion device for inserting material into a body cavity, including an elongate, tubular holder, shaped for insertion into the body cavity and having an expulsion end from which the material is expelled, and an elongate, tubular plunger, adapted to hold telescopically at least a portion of the material to be inserted. A portion of the distal end of the holder is folded under, and the plunger includes a plurality of petals at its proximal end, at least one of which is folded back for engagement with the folded under portion, to retain the plunger tube within the holder tube.

Advantageously, the applicators of the device may be completely formed from paper laminate, without the need to form slots or tabs which weaken the applicator and give it an unattractive appearance.

The term "distal end" as used herein, refers to the end of each element which is opposite the expulsion end.

Other features of the invention will be apparent from the following description of preferred embodiments and from the claims.

BRIEF DESCRIPTION OF THE DRAWINGS

FIG. 1 shows a compact tampon applicator according to one embodiment of the invention.

FIG. 2 shows a side cross-sectional view of the applicator of FIG. 1, enlarged to show detail.

FIG. 3 shows a side cross-sectional view of the applicator of FIG. 1 with the plunger in its extended position.

FIGS. 4 and 5 show detailed views of area A in FIG. 3, according to alternate embodiments of the invention.

FIG. 6 is a partial cross-sectional side view of a compact tampon applicator according to an alternate embodiment of the invention.

FIG. 7 is a partial cross-sectional side view of a compact tampon applicator according to another alternate embodiment of the invention, during assembly.

FIG. 7A is a side view of the tampon and plunger used in the applicator shown in FIG. 7.

FIG. 7B is a side view of the applicator shown in FIG. 7, after final assembly.

FIG. 11 is a cross-sectional side view of a portion of a compact applicator according to another alternate embodiment of the invention.

FIG. 12 is a side view of a compact applicator according to another alternate embodiment of the invention.

DESCRIPTION OF THE PREFERRED EMBODIMENTS

Figure 8:
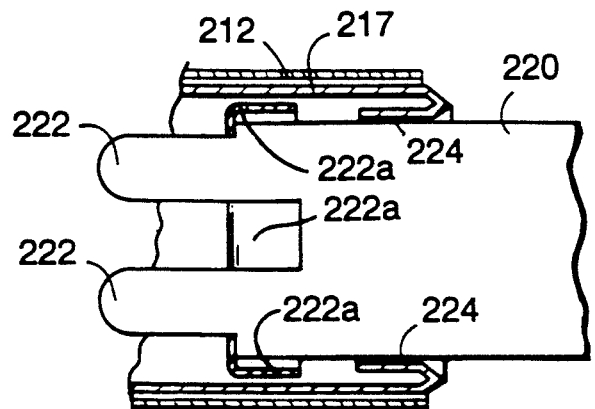
FIG. 8 is a cross-sectional side view of a portion of a compact applicator according to another alternate embodiment of the invention.

An applicator according to a preferred embodiment of the invention is shown in FIGS. 1-3. The applicator comprises tubular tampon holder 12, retaining tube 17, adhered to the inner surface of holder 12, and plunger 20, telescopically and slidably mounted inside of retaining tube 17. Tampon 13 is retained within plunger 20, with its head 11 extending over and engaging edge 15 of retaining tube 17, so that when plunger 20 is pulled back tampon 13 will remain in place. Tampon withdrawal cord 23 extends out of distal end 22 of the applicator. Expulsion end 14 of holder 12 comprises a plurality of petals 16. Preformed hinge or groove 18 is disposed circumferentially at the base of the petals. Circumferential indentations 19 and 21 are embossed into holder 12 and plunger 20, respectively, at their distal ends, to provide gripping surfaces for the user. These indentations are typically relatively shallow.

FIG. 3 illustrates the applicator in its extended position, subsequent to the user withdrawing plunger 20 to its extended portion, and prior to reinsertion of the plunger 20 to expel tampon 13. One problem which may occur during reinsertion of the plunger is "repositioning", i.e. the plunger sliding back over the tampon instead of engaging the distal end of the tampon to expel it. This problem may be solved by providing petals on the plunger tube, which close up when the plunger tube is pulled back and removed from around the tampon; by slightly flaring the distal end of the tampon during compression so that the plunger cannot easily slide over the flared end; by a tab or protrusion in a small area of the retaining structure which would force the plunger and/or tampon slightly off center; or by a small diameter plunger, as shown in FIG. 7a and described below. Other methods could also be used.

As shown in detail in FIGS. 4 and 5, plunger 20 has a raised ring 25, which interlocks with locking ring 26 disposed at the distal end of retaining tube 17. (If retaining tube 17 does not extend to the distal end of holder tube 12, locking ring 26 may be disposed instead at the distal end of holder tube 12.) This locking ring may be formed by crimping in the end of tube 17 (generally by swaging), as shown in FIG. 5, or by embossing as shown in FIG. 4. The engagement of raised ring 25 and locking ring 26 reduces the likelihood that plunger 20 will be pulled entirely out of the applicator when it is moved into its extended position, as shown in FIG. 3. Other combinations of crimped and/or embossed areas may be utilized to provide interlocking, and the raised areas may be formed by a tape or molded water-soluble material, as long as the interlock provided is sufficient to withstand the force created by the user pulling the plunger back. The plunger of the compact applicator is much more likely to come out than a non-compact plunger, which is not typically pulled back, so it is necessary to provide a more positive interlock than is generally provided in non-compact applicators.

In the embodiment shown in FIGS. 1-3, retaining tube 17 is adhered to outer tube 12, so that it remains firmly in place when plunger 20 is moved to its extended position. The adhesive is preferably a water-based adhesive, to allow the layers to delaminate when the applicator is exposed to water, thereby permitting the applicator to be disposed of by flushing. The water-based adhesive also preserves the biodegradability of the product. Suitable adhesives include, for example, dextrin and polyvinyl acetate, with polyvinyl acetate being preferred for its ability to resist delamination under humid storage conditions. Suitable polyvinyl acetate adhesives are commercially available from Findley Adhesives, Wauwatosa, WI. In an alternate embodiment, shown in FIG. 9, a circumferential reservoir 206 is provided on retaining tube 217, and a corresponding channel 208 is provided on outer tube 212, to collect any excess adhesive which is squeezed down the length of the retaining tube during assembly. Channel 208 need not be a continuous channel extending around the circumference, as shown, but could instead comprise, e.g., a plurality of reservoirs, substantially equally spaced around the circumference.

The tampon may be any radially or axially compressed tampon having a swelled "head" area. It is preferred, for complete flushability and biodegradability, that the tampon holder, retaining tube and plunger are made of laminated paper. However, if desired, any of the three tubes may be of a different material, e.g. a conventional thermoplastic or a water soluble polymer, such as the water soluble modified polyvinyl alcohol commercially available from Air Products, Allentown, PA, under the tradename VINEX. The laminated paper used in the holder tube and plunger tube is preferably a laminate of groundwood paper, for economy, with an outer layer of bleached Kraft or other white paper, for aesthetic purposes. The retaining tube, because it is not visible to the consumer, is preferably all groundwood paper. The outer surface of the tube may have a coating disposed thereon to provide improved water resistance, slip and aesthetic characteristics. This coating may be a wax coating, as is known in the art. The paper laminate may include an inner or outer layer of cellophane or thermoplastic, as disclosed in copending U.S. Ser. No. 07/819,703.

The retaining tube is preferably constructed from 1 to 3 plys of paper, preferably two plys, and has a thickness of from about 0.005" to 0.022", more preferably about 0.010". The outer surface of the plunger is preferably spaced from the inner surface of the retaining tube by about 0.004" to 0.015". The interference fit between raised ring 25 and the retaining tube, and between locking ring 26 and the plunger tube, is about ±0.005". It is preferred that the interference fit be adequate to provide a disassembly force of at least 500 grams, measured by a Hunter Spring Force Gauge.

A preferred process for assembling the applicator shown in FIGS. 1-3 is as follows: (a) the plunger is inserted into the retaining tube, expulsion end first; (b) the tampon is inserted, distal end first, into the expulsion end of the plunger, (c) adhesive is applied to the outside of the retaining tube, using any conventional coating process; (d) the retaining tube is inserted, expulsion end first, into the tampon holder; and (e) the adhesive is allowed to set.

FIG. 6 shows an alternate embodiment of the invention, in which retaining tube 17 is replaced by retaining ring 117. As with retaining tube 17, retaining ring 117 is adhered to the inner surface of holder tube 12, preferably by a water-based adhesive. The ring may be any desired length, with about 0.125 to 0.375 inches being preferred. Instead of a complete ring, as shown, the retaining structure may be a C-shaped member (an open ring), adhered to the inner surface of the holder tube.

The use of a retaining ring, or C-shaped member, in place of a retaining tube requires less material (adhesive and retaining structure material), but may make the applicator more difficult to manufacture.

Also as shown in FIG. 6, rings may be adhered onto plunger 20, distally of its expulsion end, preferably about 0.625" from the expulsion end, and near the distal end of holder 12 to provide the interlocking of the plunger and the holder. In FIG. 6, locking ring 126 replaces locking ring 26, shown in FIGS. 4 and 5, and raised ring 125 replaces raised ring 25. These rings may provide more positive interlocking than could be obtained by embossing or crimping in, since both of these processes can only deform the paper laminate to a limited extent, while the thickness of the rings can be easily varied.

An applicator having a retaining ring could be manufactured by providing a retaining ring having an outer diameter smaller than the inner diameter of the holder tube, forming a lengthwise slit in the ring, covering the outer surface of the ring with adhesive, placing the ring inside the holder tube at a desired location, and opening the slit so that the ring spreads to fit, and adhere to, the inner wall of the holder tube. Other methods of manufacture may be determined by those skilled in the art.

FIG. 7 shows another embodiment of the invention. In this embodiment, the distal end of holder tube 112 tapers to an area 114 of smaller cross-section. Slots 128, which have a "pencil" shape, i.e., elongated straight walled slots each having a pointed top, in area 114 allow the paper laminate to taper, and also allow tampon 13 and retaining tube 17 to be inserted into holder tube 112. It is preferred that the total length of each slot be about 0.69", with the length of the straight sided portion being about 0.53", and the length from the base to the tip of the pointed portion being about 0.16". After assembly, slots 128 are retained in closed position by surrounding area 114 with closing ring 113, having indentations 115, as shown in FIG. 7B. Closing ring 113 is preferably a cardboard or paper ring, as shown. Alternatively, the ring may be formed of tape. If it is a cardboard or paper ring, the ring is preferably glued or mechanically locked in place, to prevent accidental removal during use or storage. Because the distal end of the holder tube is tapered, it is not necessary in this embodiment to adhere retaining tube 17 to the inside surface of holder tube 12. Retaining tube 17 preferably extends from the base of petals 16 to the beginning of tapered area 114, so that the tapered area provides a positive stop which holds the retaining tube in place when the plunger is pulled back. (If a shorter retaining tube is provided, the tube and tampon will initially move backward until the distal end of the retaining tube engages the tapered area, and then will be retained in place.)

FIG. 7A shows another feature of the embodiment shown in FIG. 7. Instead of plunger 20, shown in FIGS. 1-3 and 6, which has an inner diameter which is slightly larger than the diameter of the tampon, plunger 120 has an inner diameter that is slightly *smaller* than the diameter of the tampon. In order to insert the tampon into plunger 120, slit 130 is provided lengthwise in plunger 120. Slit 130 preferably comprises angled region 132, which facilitates opening up of the slit without tearing of the paper laminate. The angle formed by region 132 is preferably greater than 90 degrees, more preferably between 100 and 150 degrees. Slit 130 is at least the length of the tampon, so that the tampon can be inserted into plunger 120, and is preferably slightly longer. When tampon 13 is retained within plunger 120, slit 130 is open. When plunger 120 is pulled back into its extended position, slit 130 closes, aided by the passage of plunger 120 through tapered area 114. Accordingly, repositioning is avoided by the smaller cross-section of plunger 120, which does not allow it to slide back over the tampon once slit 130 has closed. To further prevent repositioning, an inwardly folded tab or other protrusion may be included on the retaining tube to move the plunger and/or tampon off center (not shown). It is preferred that this tab or protrusion extend inwardly about 0,015" to 0.030". Plunger 120 also has nibs 131, which prevent the plunger from falling out of the holder tube, and help to close the slit in the plunger during withdrawal of the plunger to its extended positions.

A small cross-section, slitted plunger, like plunger 120, may also be utilized in other, non-tapered embodiments, if desired. (It is generally necessary in the embodiment of FIG. 7 because a large cross-section plunger would not fit inside tapered area 114.) However, the slit is especially adapted for use in the tapered embodiment of FIGS. 7-7B, after prolonged storage the paper of the plunger may relax and passing the slit portion of the plunger through the tapered area will assist in properly closing slot 130 so that it properly engages the tampon.

Figure 9:
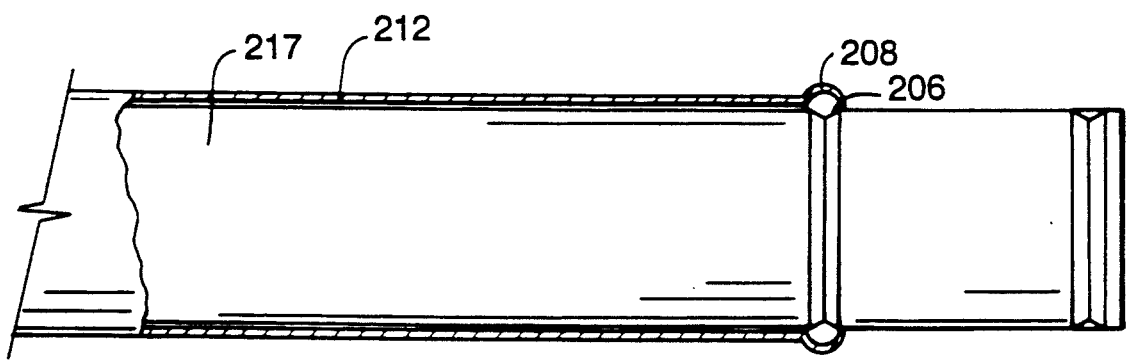
FIG. 9 is a cross-sectional side view of a portion of a compact applicator according to another alternate embodiment of the invention.

While preferred embodiments have been described above, other variations and modifications are within the scope of the following claims. For example, as shown in FIGS. 9 and 10, the retaining tube may be longer than the holder tube, and a short holder tube may be used, providing a small diameter, aesthetically appealing applicator with a convenient area for finger gripping.

Additionally, as shown in FIG. 8, inadvertent removal of the plunger from the applicator can be avoided by providing a plunger 220 having petals 222 and 222a. (These petals also prevent repositioning.) While petals 222 remain in their normal position, to prevent repositioning, alternating petals 222a are bent back, so that they engage a folded-under portion 224 of retaining tube 217. This means of retaining the plunger within the holder may be used in other types of compact and standard tampon applicators, in addition to the applicators described herein.

Figure 10:
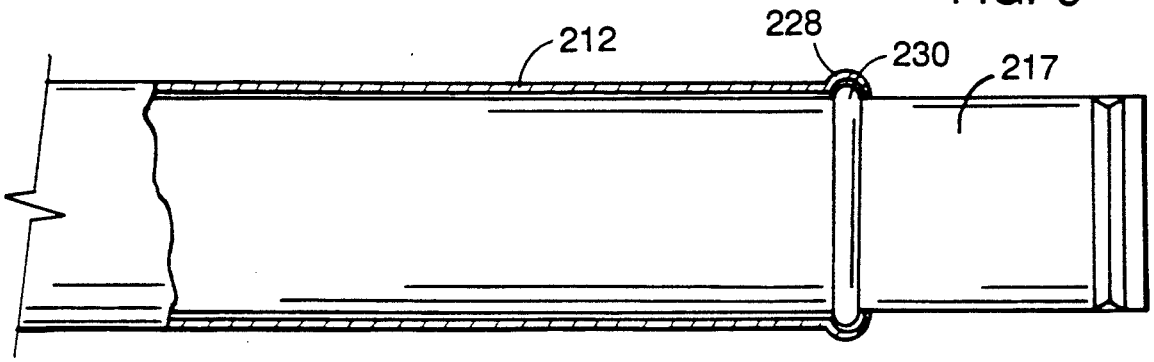
FIG. 10 is a cross-sectional side view of a portion of a compact applicator according to another alternate embodiment of the invention.

Further, as shown in FIG. 10, instead of, or in addition to, securing the retaining tube in the holder by adhesive, it can be secured by providing a raised area, e.g., a raised ring 230, on retaining tube 217, and a corresponding channel 208 of holder 12 to receive the raised area. The engagement of the raised area and the channel serves to securely hold the retaining tube in place, obviating the need for adhesive.

As shown in FIG. 11, crimps 30 may be formed in retaining tube 17 to enable the retaining tube to more positively retain the tampon in place when the plunger tube is pulled back. Any number of crimps may be used; 3 crimps at 120 degree intervals or 4 crimps at 90 degree intervals (as shown) are preferred.

As shown in FIG. 12, the distal end of the plunger tube may include a rim 32, preferably formed by curling the paper laminate outwardly. This smooth rim provides a more positive finger grip for the user.

I claim:

1. An insertion device for inserting material into a body cavity, said material having an enlarged head portion, comprising;

an elongate, tubular holder, comprising at least one layer of paper, said holder being shaped for insertion into the body cavity and having an expulsion end which is dimensioned to fit over the head portion of the material and adapted to open to allow said material to be expelled therethrough;

an elongate, tubular plunger, adapted to hold telescopically at least a portion of the material to be inserted, dimensioned to fit telescopically and slidably within said holder and to be movable from a telescoped position in which a major portion of said tubular plunger is within said holder to an extended position in which one distal end of the plunger is withdrawn from the tubular holder, and adapted, in said extended position, to expel said material from said device when pushed manually into said holder; and a retaining structure, comprising a member separate from said holder tube, said member being interposed between said plunger and said holder and mounted on an inner surface of said holder tube at said expulsion end to engage the head portion of said material and prevent it from moving with said plunger when said plunger is moved from said telescoped to said extended position.

2. The device of claim 1 wherein said material is a tampon and said holder is shaped for vaginal insertion.

3. The device of claim 2 wherein said retaining structure is an elongate tube.

4. The device of claim 3 wherein said tube extends from the base of said head portion to the distal end of said holder.

5. The device of claim 2 wherein the holder has a stop on its inner surface, disposed near its distal end, and the plunger has a corresponding raised area at its expulsion end, such that the stop and raised area interlock to resist withdrawal of the plunger tube from the holder tube.

6. The device of claim 2 or 4 wherein the retaining structure has a stop on its inner surface, disposed near its distal end, and the plunger has a corresponding raised area distally of its expulsion end, such that the stop and raised area interlock to retain the plunger tube within the holder tube when it is withdrawn prior to use.

7. The device of claim 2 wherein the retaining structure is a ring or C-shaped member adhered to the inner surface of the tampon holder tube, disposed adjacent the head of the tampon to retain the tampon when the plunger tube is withdrawn.

8. The device of claim 5 wherein said stop is a ring or C-shaped member adhered to the inner surface of the tampon holder tube at its distal end and said raised area is a ring or C-shaped member adhered to the outer surface of the plunger, distally of its expulsion end.

9. The device of claim 6 wherein said stop is a ring or C-shaped member adhered to the inner surface of the retaining structure and said raised area is a ring or C-shaped member adhered to the outer surface of the plunger, distally of its expulsion end.

10. The device of claim 2 wherein said retaining structure is adhered to the inner surface of said holder by an adhesive.

11. The device of claim 10 wherein said retaining structure is adhered by a water-based adhesive.

12. The device of claim 10 wherein said retaining structure includes a reservoir for containing excess adhesive.

13. The device of claim 12 wherein said holder includes a channel disposed in opposing spaced relation to said reservoir.

14. The device of claim 2 wherein a portion of the distal end of the retaining structure is folded under, and the plunger includes a plurality of petals at its proximal end, at least one of which is folded back for engagement with said folded under portion to retain the plunger tube within the holder tube when the plunger is withdrawn prior to use.

15. The device of claim 2 wherein said retaining tube includes a raised area which engages a channel in said holder tube, to secure said retaining tube within said holder.

16. The device of claim 2 wherein said retaining structure has a thickness of from about 0.005" to 0.022".

17. The device of claim 2 wherein the outer surface of the plunger is spaced from the inner surface of the retaining tube by about 0.004" to 0.015".

18. The device of claim 2 wherein the plunger has an outer diameter smaller than the outer diameter of the tampon, and is slitted to allow the tampon to be retained therein.

19. The device of claim 2 wherein the retaining structure includes at least one portion which extends radially inward disposed circumferentially at an end of said retaining structure closest to the expulsion end of said holder.

20. The device of claim 19 wherein said portion is a crimp.

21. The device of claim 20 wherein said retaining structure includes at least three circumferentially spaced crimps.

22. The device of claim 2 wherein said distal end of said plunger includes a circumferential rim.

23. An insertion device for inserting material into a body cavity, said material having a head portion, comprising;
   an elongate, tubular holder comprising at least one layer of paper, said holder, being shaped for insertion into the body cavity and having an expulsion end of a first diameter, which is dimensioned to fit over the head portion of the material and adapted to open to allow said material to be expelled therethrough, and a distal end having a plurality of strips which, when urged together, form a portion having a second diameter, smaller than said first diameter;
   a closing ring, surrounding said portion and retaining said strips together; and
   an elongate, tubular plunger, adapted to hold telescopically at least a portion of the material to be inserted, dimensioned to fit telescopically and slidably within said holder and to be movable from a telescoped position in which a major portion of said tubular plunger is within said holder to an extended position in which one distal end of the plunger is withdrawn from the tubular holder, and adapted, in said extended position, to expel said material from said device when pushed manually into said holder.

24. The device of claim 23 wherein said material is a tampon, said head portion is enlarged relative to the rest of the material, and said holder is shaped for vaginal insertion.

25. The device of claim 24 further comprising a retaining structure, interposed between said plunger and said holder and disposed at said expulsion end to engage the head portion of said material and prevent it from moving with said plunger when said plunger is moved from said telescoped to said extended position.

26. The device of claim 24 or 25 wherein the plunger has an outer diameter smaller than the outer diameter of the tampon, and is slit to allow the tampon to be retained therein.

27. The device of claim 26 wherein the slit extends longitudinally from the expulsion end of the plunger toward the distal end of the plunger, defining a longitudinal region.

28. The device of claim 27 wherein an angled region of said slit extends from the distal end of said longitudinal region circumferentially around said plunger.

29. The device of claim 28 wherein the angle formed between said longitudinal region and said angled region of said slit is at least 90 degrees.

30. An insertion device for inserting material into a body cavity, comprising:
   an elongate, tubular holder, shaped for insertion into the body cavity and having an expulsion end from which the material is expelled; and
   an elongate, tubular plunger, adapted to hold telescopically at least a portion of the material to be inserted;
   wherein a portion of the distal end of the holder is folded under, and the plunger includes a plurality of petals at its proximal end, at least one of which is folded back for engagement with said folded under portion, to retain the plunger tube within the holder tube.

31. The device of claim 30 wherein said material is a tampon and said holder is shaped for vaginal insertion.

32. The device of claim 31 wherein said plunger is dimensioned to fit telescopically and slidably within said holder and to be movable from a telescoped position within said holder to an extended position in which one distal end of the plunger is withdrawn from the distal holder, and adapted, in said extended position, to expel said material from said device when pushed manually into said holder.

33. The device of claim 31 wherein alternating petals are folded back.

34. An insertion device for inserting material into a body cavity, said material having an enlarged head portion, comprising:
   an elongate, tubular holder, comprising at least one layer of paper, said holder being shaped for insertion into the body cavity and having an expulsion end which is dimensioned to fit over the head portion of the material and adapted to open to allow said material to be expelled therethrough;
   an elongate, tubular plunger, adapted to hold telescopically at least a portion of the material to be inserted, dimensioned to fit telescopically and slidably within said holder and to be movable from a telescoped position in which a major portion of said tubular plunger is within said holder to an extended position in which one distal end of the plunger is withdrawn from the tubular holder and adapted, in said extended position, to expel said material from said device when pushed manually into said holder; and
   a retaining structure, comprising an elongate tube adhered to an inner surface of said holder and disposed at said expulsion end to engage the head portion of said material and prevent it from moving with said plunger when said plunger is moved from said telescoped to said extended position.

35. An insertion device for inserting material into a body cavity, said material having an enlarged head portion, comprising;

an elongate, tubular holder, comprising at least one layer of paper, said holder being shaped for insertion into the body cavity and having an expulsion end which is dimensioned to fit over the head portion of the material and adapted to open to allow said material to be expelled therethrough;

an elongate, tubular plunger, adapted to hold telescopically at least a portion of the material to be inserted, dimensioned to fit telescopically and slidably within said holder and to be movable from a telescoped position in which a major portion of said tubular plunger is within said holder to an extended position in which one distal end of the plunger is withdrawn from the tubular holder, and having a plurality of petals at its proximal end, said petals adapted to engage said material when said plunger is in said extended position, to expel said material from said device when said plunger is pushed manually into said holder; and a retaining structure, interposed between said plunger and said holder and disposed at said expulsion end to engage the head portion of said material and prevent it from moving with said plunger when said plunger is moved from said telescoped to said extended position.

* * * * *